United States Patent [19]
Streiff et al.

[11] Patent Number: 4,956,186
[45] Date of Patent: Sep. 11, 1990

[54] PROCESS FOR THE PRODUCTION OF LOW CALORIE YOGURT

[75] Inventors: Paul J. Streiff, Camillus; David L. Hoyda, Baldwinsville; Edward Epstein, Manlius, all of N.Y.

[73] Assignee: Borden, Inc., Columbus, Ohio

[21] Appl. No.: 427,185

[22] Filed: Oct. 25, 1989

[51] Int. Cl.$^5$ .................. A23C 9/133; A23C 9/137; A23L 1/236
[52] U.S. Cl. .................................... 426/43; 426/583; 426/548; 426/491; 426/495; 426/61
[58] Field of Search ................. 426/43, 61, 583, 548, 426/491, 495, 42, 634

[56] References Cited

U.S. PATENT DOCUMENTS

| | | |
|---|---|---|
| 1,737,101 | 11/1929 | Turnbow . |
| 4,228,189 | 10/1980 | Henson et al. ............... 426/40 |
| 4,430,349 | 2/1984 | Malone et al. ............... 426/34 |
| 4,626,441 | 12/1986 | Wolkstein ............... 426/548 |
| 4,689,245 | 8/1987 | Kosikowski et al. ............... 426/72 |
| 4,837,035 | 6/1989 | Baker et al. ............... 426/548 |
| 4,837,036 | 6/1989 | Baker et al. ............... 426/43 |

FOREIGN PATENT DOCUMENTS 197711 7/1974 Canada .
2224096 10/1974 France .
8809125 12/1988 PCT Int'l Appl. .

OTHER PUBLICATIONS

"Ultra-Filtration: An Emerging Unit Operation" Chemical Engineering, p. 170, May 9, 1978.
Engle, "The Use of Lactase to Sweeten Yogurt Without Increasing Calories", Cult. Dairy Prod. J. 8:6.
O'Leary 1976 J. Food Sci. 41:791.

*Primary Examiner*—Marianne Cintins
*Attorney, Agent, or Firm*—Dennis H. Rainear; Kenneth P. Van Wyck

[57] ABSTRACT

The invention is directed to a process for preparing reduced calorie, essentially lactose free, artificially sweetened yogurt. By utilizing ultrafiltration and enzymatic hydrolysis to reduce the lactose content, and by the addition of low calorie sweeteners, a yogurt product is produced with 60–70 calories per six ounces of product. Because the lactose level is reduced to less than 0.1% by weight, the product is amenable to lactose-intolerant individuals.

26 Claims, No Drawings

PROCESS FOR THE PRODUCTION OF LOW CALORIE YOGURT

FIELD OF THE INVENTION

The invention relates to a process for the production of low calorie, artificially sweetened yogurt which is essentially lactose-free.

BACKGROUND OF THE INVENTION

Yogurt is a product which results from incubating milk, partly skimmed milk, or skimmed milk with a yogurt culture with or without added non-fat milk solids. This cultured dairy food is made by fermenting milk with cultures of the microorganisms *Lactobacillus bulgaricus* and *Streptococcus thermophilus*. This fermentation results in a spoonable custard-like milk product having somewhat of a firm body similar to light bodied pudding. Yogurt has a clean, distinct acid taste and cultured milk flavor resulting from the fermentation process.

Prior development and technology in yogurt making processes has resulted in yogurt with lower calories. The methods previously utilized for producing low calorie yogurt have included the reduction or elimination of sweeteners replacing them with artificial non-nutritive sweeteners such as aspartame and saccharin.

Reducing the caloric content of yogurt even further can result in a product having a weak body and/or poor flavor if it involves an extreme reduction in the overall solids of the yogurt. A simple reduction in the milk solids not only results in a weak bodied product but also one that is nutritionally inferior, especially with regard to the protein content.

In the conventional process of making yogurt, pasteurized milk, either with or without added non-fat milk solids, is inoculated with a culture of yogurt organisms and incubated at a temperature of 104° to 113° F. The growth of the organisms at the incubation temperature produces lactic acid. When sufficient acid has been formed to lower the pH of the incubating admixture to about 5.0, the casein in the admixture begins to flocculate and form a gel. Bacterial growth and acid development continue in yogurt manufacture until a pH in the range of about 4.5 to 3.5 is reached. In plant operation, satisfactory incubation or bacterial growth usually requires about three to seven hours. In order to preclude further acid development and bacterial growth in the yogurt product resulting from the incubation step, it is refrigerated at a temperature in the range of 30° F. to 50° F. Refrigeration not only stops the growth of the organisms but also firms up the resulting yogurt gel.

Yogurt can be sweetened without increasing its caloric content by either of two routes. The lactose present in a given yogurt product can be subjected to enzymatic digestion by lactase, resulting in the production of sugars such as glucose which impart greater sweetness. Lactase or beta-galactosidase or beta-galactopyranosidase is a very specific enzyme which splits the disaccharide lactose into the two monosaccharides, glucose and galactose. It is desirable that the lactase be free of other enzymes which would be active in the milk system, such as proteases which could cause off-flavors and enzymes which would result in fermentation of the glucose with the formation of alcohol.

The hydrolysis of a lactose in the presence of a lactase enzyme is known. The Turnbow patent No. 1,737,101, which was issued in 1929, describes hydrolysis of lactose by lactase enzyme to produce sugars which are more water-soluble than lactose. This feature allows incorporation of more milk solids and production of frozen milk products having improved quality.

Alternatively, increased sweetness is conventionally achieved by the addition of an artificial sweetener such as aspartame, cyclamate or saccharin to the yogurt.

As will be shown hereinafter, added sugar can be entirely eliminated from sweetened yogurt by using ultrafiltered lactase treated skim milk and an artificial sweetener. This aspect magnifies the desirable attribute of reducing calories in a sweetened yogurt since in total absence of added sugar, the caloric reduction by the present invention is up to 33%.

It is frequently difficult or unsatisfactory to apply the first technique of sweetening, i.e., enzymatic digestion of lactose, to a diluted ultra-filtered skimmed milk because of its low lactose content. However, alternatively leaving the lactose level high produces a product which is not digestible by lactose intolerant ethnic groups or individuals.

A significant proportion of the world's population is unable to digest the disaccharide lactose due to a deficiency of lactase in the intestinal mucosa. Approximately 60–90% of non-Caucasian people have low lactase activity. This inability to digest lactose may result in the manifestation of symptoms such as stomach cramps, flatulence and diarrhea when milk and certain other dairy products are consumed. Commercial yogurts frequently contain appreciable amounts of lactose due to the practice of fortifying the yogurt mix with non fat milk solids.

In addition, the market for yogurt is somewhat limited in that many people do not enjoy its characteristic sharp acid flavor. Attempts to improve the flavor of yogurt made in the conventional way have not been entirely satisfactory. The addition of sugar and flavors, particularly fresh pureed fruits and berries, to the mix undergoing the incubation stage has met with disfavor in that the incubation conditions cause loss of flavor and color in the flavoring additives.

It is known to prepare cultured milk products by membrane filtration of milk and similar liquid milk products containing coagulable protein to concentrate the protein content before the protein is coagulated by incubation. The pressure applied to effect membrane filtration cannot exceed the osmotic pressure of the solution. Where this pressure is considerable, such as in solutions of solutes of similarly small dimensions, the process is usually known as reverse osmosis. When solutions of substantially bigger and generally organic molecules such as proteins are involved, the term ultrafiltration is usually applied to the process.

In Chemical Engineering Publication "Ultra-filtration: An Emerging Unit-operation" May 9, 1978 at page 170, second column, ultrafiltration is taught for concentration of proteins in skim milk for the production of a low fat yogurt.

The French Patent Publication, FR No. 2,224,096, relates to the preparation of yogurt from ultrafiltered milk said to have high protein and low lactose contents. The invention of the French patent is directed to improvement of the storage life and stability of yogurt by a reduction in the fermentable lactose content, which reduces the content of lactic acid formed by lactose fermentation.

The Kosikowski U.S. Pat. No. 4,689,245 issued Aug. 25, 1987 relates to a coffee whitener composition made from milk ultrafiltration retentate. Kosikowski et al. disclose an ultrafiltration process which utilizes a membrane which passes water, lactose and other soluble milk components but retains milk proteins and fats (column 2, line 15). Kosikowski et al. do not disclose a yogurt making process.

The Henson U.S. Pat. No. 4,228,189, issued Oct. 14, 1980, relates to the preparation of yogurt utilizing a semi-permeable membrane to reduce minimal salt content and concentrate protein content of milk. Henson et al. indicate that ultrafiltration connotes the application of a semi-permeable membrane to separate solutions of large organic molecules such as proteins (U.S. Pat. No. 4,228,189, column 1, line 40). In the example, Henson, et al. discloses concentrating protein in fresh milk with a membrane; however, the lactose concentration remained unchanged after application of the membrane.

The Canadian Patent, CA No. 197711 relates to a naturally sweetened yogurt having a low calorie content. The patent discloses the addition of a lactase enzyme to a milk product in order to convert lactose in the yogurt to simple sugars which are more soluble in water and are also sweeter than lactose. Glucose and galactose are the principle sugars.

Other publications that disclose the use of lactase treated milk in yogurt production include:

Engle, W. G. 1973. "The Use of Lactase to Sweeten Yogurt Without Increasing Calories". Cult. Dairy Prod. J. 8:6; and Leary, V. S. and J. H. Weychik. 1976. "A Comparison of Some Chemical Properties of Yogurts Made From Control and Lactase-Treated Milks." J. Food Sci. 41:791.

The PCT Patent Publication WO No. 88/09125 relates to a low calorie, low fat yogurt product prepared by a process which included adding a nutritive sweetener. Claims 6 and 7 recite aspartame as a nutritive sweetener.

The Wolkstein U.S. Pat. No. 4,626,441, issued Dec. 2, 1986, relates to the use of aspartame in dietetic frozen yogurt or dietetic yogurt comprising: as the sweetener, mixtures of aspartame with synergistic sweetener or aspartame alone; in combination with yogurt cultures and a bulking agent. Wolkstein further discloses the addition of lactase to convert lactose to glucose and galactose. See column 2, line 47.

The Malone U.S. Pat. No. 4,430,349 issued Feb. 7, 1984, relates to an artifically sweetened yogurt prepared by mixing a stabilizer solution containing high methoxyl pectin, low methoxyl pectin and aspartame with prepared yogurt.

An object of the present invention is a process for the production of low calorie, low lactose yogurt.

It is a further object of the present invention to produce a low calorie, low lactose yogurt by a combination of ultrafiltration, enzymatic cleavage of lactose, and addition of an artificial sweetener.

The present invention is related to the invention described in copending patent application U.S. Ser. No. 413,200 filed Sept. 27, 1989 and assigned to the same assignee as the present invention. The invention of U.S. Ser. No. 413,200 is directed to the use of added fiber in yogurt to reduce calories and increase dietary fiber. The U.S. Ser. No. 413.200 application is incorporated herein by reference, and the techniques of cooking the fiber with a fruit filling and adding the cooked fiber and fruit to yogurt is also operative in the present invention.

SUMMARY OF THE INVENTION

The invention is directed to the combination of three technologies which when combined produce an improved process for preparing yogurt. The yogurt produced by the present invention is a low calorie, artificially sweetened product, with very low levels of lactose, a feature of great importance to the vast number of lactose-intolerant consumers. The invention comprises the steps of (1) ultrafiltration of skim milk to concentrate the milk, which after dilution results in a decrease of the lactose content of the resulting yogurt base (2) adding a lactase enzyme to the yogurt base and culture to further reduce the lactose content, (3) sweetening the resulting yogurt with an artificially sweetened flavoring.

The term "skim milk" is used generically in the specification and claims to refer not only to skim milk and partially skim milk, but also to the lactose-containing products derived from any of the above milks, including whey derived from casein or cheese manufacture, the mother liquor wash water obtained as a waste product in the production of lactose from whey or skim milk products, and lactalbumin mother liquor such as those obtained following the precipitation of lactalbumin. All skim products which contain lactose can be treated by the process of the invention to reduce the lactose content thereof.

The invention is particularly applicable to cows' milk, however, the term "milk" as commonly used refers to the normal secretion of the mammary glands of a mammal. All milks contain an appreciable lactose content. The process of the invention may be employed to reduce the lactose content without reducing the total sugar content of any milk including, in addition to cows' milk, mares' milk, goats' milk, ewes' milk, etc.

DETAILED DESCRIPTION OF THE INVENTION

The invention is directed to a process for preparing reduced calorie, artificially sweetened yogurt comprising: (a) concentrating skim milk by ultrafiltration whereby at least a portion of the lactose, riboflavin and certain water soluble species are removed into the permeate (b) adding water to the ultrafiltered skim milk retentate of step (a) whereby the lactose level is decreased; (c) subjecting the product of step (b) to temperature and pressure sufficient to homogenize the product; (d) subjecting the product of step (c) to temperature sufficient to pasteurize the product, and cooling the product; (e) culturing the product of step (d) by adding a sufficient amount of a lactase enzyme to the product, and inoculating the mixture with a sufficient amount of a yogurt culture, and allowing the mixture to incubate until the pH of the mixture reaches about 4.50; (f) adding an artificially sweetened flavoring to the cultured mixture of step (e).

In another embodiment of the process of the present invention, the skim milk is pasteurized before being circulated or recirculated through the ultrafiltration unit. In such an embodiment, the pasteurized skim milk is maintained at a temperature of 35°–45° F. while being recirculated through the ultrafiltration unit until concentrations of the solids in the milk are increased 3 to 4 fold, or from approximately 9% total solids to 27–36% total solids.

In a preferred embodiment of the present invention, the ultrafiltration of the skim milk is achieved by cooling the skim milk to 40° F. or below and passing it singularly or repeatedly through the UF membrane, module or unit. The UF step of the present process can be done at a temperature as high as about 140° F. (60° C.), with higher temperatures generally increasing the flux. However, high temperature$ can create deleterious effects on the product such as occassional off flavors or spoilage due to microbial growth.

The temperature can be maintained by passing the milk through a cooler or by holding the milk in a jacketed kettle with cooling water applied. Operation of the ultrafiltration process can be done at temperatures up to, for example, 158° F. (70° C.) and feed pressures of up to 220 psi (15 bar).

More specifically, skim milk is, according to the present invention, concentrated by ultrafiltration through a semipermeable membrane.

In ultrafiltration, solution components are separated on the basis of molecular size and shape. Under an applied pressure across an ultrafiltration membrane, solvent and small solute species pass through the membrane and are collected as permeate while larger solute species are retained by the membrane and recovered as a concentrated retentate. Unlike reverse osmosis, ultrafiltration allows passage of lower molecular weight species. Typically the solute molecules to be concentrated in ultrafiltration are likely to be 10 or more times larger than those of the solvent.

Ultrafiltration membranes useful in the present invention can include but are not limited to films of for example cellulose acetate, polyamide, polysulfone, polyacrylonitrile and polyfuran. Other known ultrafiltration materials are also operative herein. Hollow fiber membranes or modules are particularly effective in the process of the present invention. The UF unit can be a tubular, plate, spiral design, all of which are conventional and known to those skilled in the art. It is preferred but not required in the present invention that the feed stream flows through the lumen of a hollow fiber UF unit. In order to control concentration polarization and to maintain efficient operation, it is preferred herein that the feed stream of skim milk be passed over the membrane surface, or through the hollow fiber lumen, at high velocity. This means that the flow rate of the feed stream is much higher than the ultrafiltration rate permeating through the membrane. Since the concentration difference across the membrane for a single pass is small, the skim milk feed stream is preferably recirculated continously through the ultrafiltration module or through multiple units or modules. However, if the surface area of the UF membrane is high enough to effect sufficient concentration, single pass of the feedstream can be utilized. Thus batch operations are also operative herein.

In the present invention, skim milk having an initial total solids level of, for example, about 8.5% by weight is subjected to ultrafiltration. During the ultrafiltration, the skim milk is separated into a retentate portion which does not pass through the membrane, and a permeate portion which does pass through the membrane. In the permeate portion is found lactose, riboflavin and water soluble species approximately similar in size to lactose molecules. The retentate has become concentrated to a total solids level of about 26–30% solids and a lactose content of about 4.5% to 14.0% by weight. This retentate is then diluted back to a total solids level of about 8.25% MSNF, with a lactose level of about 1.5% to 1.6% by weight.

Thus a typical analysis of skim milk before and after ultrafiltration is as follows:

|  | Skim Milk | Retentate | Permeate |
| --- | --- | --- | --- |
| Solids | 9.20% | 28.64% | 3.51% |
| Protein | 3.41% | 14.00% | 0.13% |
| Fat | 0.18% | 0.30% | 0.06% |
| Ash | 0.76% | 2.05% | 0.37% |
| Carbohydrate (lactose) | 4.85% | 12.29% | 2.95% |

These values were obtained by passing skim milk through a ultrafiltration unit available from APV Crepaco, Inc., Chicago, Ill., at 7° C. and a pressure of 15 bar. A preferred membrane for use in the ultrafiltration unit is a polysulfone membrane from PCI MEMBRANE SYSTEMS LTD., ENGLAND with molecular weight cut-off 20,000.

Another UF membrane operative herein is the DESAL system available from DESAL Desalination Systems, Inc., Escondido, Calif. The preferred pore size of the UF membrane system is from about 5 to about 1000 Angstroms, but a more preferred range is from about 10 to 500 Angstroms.

It is preferred but not required for the present invention that the UF membrane system provides retentate comprising protein species of molecular weight higher than 10,000 and permeate comprising compounds of predominantly molecular weight lower than 400. In this manner, the protein tends to be concentrated in the retentate and the lactose tends to be concentrated in the permeate. These values, however, are not limitations in the present invention.

The skim milk feed stream is passed through the UF membrane system in a single pass or multiple passes during which the protein is concentrated within the retentate and lactose and some minerals are at least partially removed into the permeate. Continuous recirculation of the retentate increases the protein concentration and further reduces the lactose content.

The skim milk, concentrated to about 26–36% and preferably 26–28% total solids, is collected from the retentate fraction of the ultrafiltration process and then reconstituted by the addition of water. Water can be added in amounts sufficient to achieve any desired total solids level, but a preferred total solids level is from about 8.25 to 11.0 percent on a weight basis. The lactose content after dilution of the retentate level is less than 2.0% and preferably about 1.5 to 1.6% by weight. It is preferred in the present invention to achieve a milk solids not fat (MSNF) of at least 8.25%, which is the current minimum allowed under the Food and Drug Administration's standard of identity for yogurt (21 CFR 131.200).

Optional ingredients may be added to the reconstituted or partially reconstituted skim milk including but not limited to modified food starch, gelatin, cream, milk, partially skimmed milk, skim milk, nonfat dry milk, buttermilk, whey, lactalbumins, lactoglobulins, whey modified by partial or complete removal of lactose and/or minerals, Vitamin A and/or D, color additives, flavoring ingredients, and stabilizers. Nutritive carbohydrate sweeteners which can be added can include sugar, refiner's sirup, molasses, high fructose corn sirup, fructose sirup, maltose, maltose sirup, dried maltose sirup, malt extract, dried malt extract, malt sirup, dried malt sirup, honey and maple sugar. Other processing or preservative additives can also be added to the ultrafiltered skim milk. Another additive useful herein is gum arabic, such as Hitek Gum Arabic #2, available from Hitek Polymers, Clifton, N.J.

In a preferred embodiment, modified food starch and gelatin (250 bloom) are added to the ultrafiltration skim milk at levels of 0.75 weight percent and 0.50 weight percent, respectively. 250 Bloom Gelatin is a commercial preparation available from Germantown Manufacturing, Bloomall, Pa. Gelatin is derived from animal skin or hoof. Stabilizers, such as Hitek Stabilizer 689 (a blend of tapioca starch and pectin), can also be added to the yogurt base mix before or after it is reconstituted. Modified food starch is Purity W, available from National Starch and Chemical Corporation.

The yogurt product can also optionally contain fruit pieces, fruit pulp, fruit concentrate, fruit flavoring, fruit puree, fruit fiber, and the like. Additional optional additives include artificial fruit flavor and natural fruit flavor.

As mentioned earlier, the present invention can also include fiber enriched yogurts produced by the addition to the formulations of fiber such as micro sized soy fiber and the like. In this manner additional reduction of the calories per six ounce serving of yogurt product is possible by achieving a fiber loading of as high as 5.0 percent by weight. A particularly preferred embodiment is the precooking of soy fiber with the fruit base, followed by mixing this cooked product with the yogurt base and starter culture.

The yogurt produced by the process of the present invention possesses, for example, 8.25% MSNF but exhibits physical properties of high viscosity, full body, smooth, firm coagulum, and mouthfeel like the corresponding properties of a yogurt product with 10–13% MSNF. Thus by the present invention, low solids yogurt is prepared with the desirable features associated with higher solids yogurt.

The reconstituted UF skim milk, with or without additives, is preferably homogenized by conventional means. This can include, for example, heating the yogurt base mix to about 140° F. and in a single or dual stage pressurized system, produce homogenized yogurt base mix. If a dual stage pressurized homogenizing system is used, a preferred first stage pressure is about 1000 to 2000 psi while the preferred second stage is about 300–800 psi.

After the homogenization of the yogurt base mix derived from the diluted retentate of the UF operation, it is desirable to pasteurize the mix if the skim milk was not pasteurized before the ultrafiltration step. Any conventional pasteurization technique, process or method is operable in the present invention provided that charring and other off-flavor characteristics are avoided. A preferred pasteurization is achieved by maintaining the base mix at 180°—185° F. for 30 minutes.

After pasteurization, the base mix derived from the UF operation above is cooled to a temperature sufficient to support enzyme activity. A preferred incubation temperature is in the range of 65° to 135° F., and a more preferred incubation temperature is in the range from 104° to 113° F. To the cooled base mix is added a lactase enzyme, such as, but not limited to, Pfizer's Neutral Lactase (Pfizer, Milwaukee, Wis.), Lactozym 1500 L type GP or Lactozym 3000 L type HP (Novo Laboratories Inc., Wilton, Conn.). Lactozym is a beta-galactosidase preparation produced by submerged fermentation of a selected strain of the yeast *Kluyveromyces fragilis*. Pfizer Neutral Lactase is a food grade liquid lactase concentrate prepared from an extract of *Candida pseudotropicalis*, a lactose fermenting dairy yeast. Pfizer Neutral Lactase is beta-D-galactoside galactohydrolase. The amount of lactase added is determined by the initial lactose content of the yogurt mix after UF treatment, according to the present Invention, and the desired final lactose content after enzymatic treatment. It is preferred that the product produced after lactase treatment is essentially lactose free. By "lactose free" herein is meant lactose present in at most only trace amounts and preferably not present at any detectable level. A preferred lactase level useful in achieving a lactose free product is from about 0.01 to about 2.0 volume percent and a more preferred level is from about 0.05 to about 0.2% by volume. The most preferred level of lactase enzyme is that amount sufficient to reduce the lactose content to the desired lactose-free level. By the lactase enzyme step of the present invention, a lactose level in the diluted retentate from the UF treatment of, for example less than 2.0% and more preferably, 1.5 to 1.6%, can be reduced to less than 0.1%. In a preferred embodiment, the lactose content after lactase treatment of the yogurt is undetectable.

At or about the same time that the lactase is added to the yogurt mix, a yogurt starter culture is added in an amount sufficient to initiate and maintain the requisite protein coagulation. A preferred amount of yogurt culture is from 0.5 to 3% and a more preferred amount is from 1.0 to 1.5% by volume. A preferred yogurt starter culture comprises *Lactobacillus bulgaricus*, and *Streptococcus thermophilus*. In addition thereto, *Lactobacillus, acidophilus* can also be added to the culture. Yogurt starter culture is a commerical preparation available from Chris Hansen's Laboratory, Milwaukee, Wis. The mixture comprising the yogurt mix, starter culture, and lactase is allowed to culture or incubate for a period of time sufficient to cause the protein to coagulate, whereby lactic acid is produced, and the pH drops. The culturing or incubation generally takes about 2 to 4 hours. A preferred temperature range for the incubation is from 86° to 122° F. and a more preferred range is from 104° to 113° F. At about a pH of 5.0, the casein in the yogurt formulation begins to flocculate and forms a gel. When the pH achieves a level of less than about 5.0 and preferably of about 4.9 or less, the culturing is discontinued by cooling the yogurt mix to 35°—75° F. with agitation. The lactose content of the yogurt is generally reduced by this point by 90-99% relative to the initial lactose content of the skim milk.

The final step of the present invention is the addition of a non-calorie or low-calorie sweetener. One effect of the UF treatment of the skim milk is to reduce the lactose content, which content normally is responsible for the eventual caloric content and acid development of the final yogurt product. Another surprising effect of the UF treatment of skim milk in the present invention is a more acidic taste of the resulting yogurt product relative to yogurt prepared from skim milk not treated with UF.

Thus an additional sweetener is required for the present invention to produce an acceptable yogurt product. Because one of the objects of the present invention is the production of a low calorie yogurt, non-caloric and/or artifically or naturally sweetened flavoring is preferred herein. The artificial sweetener or sweeteners can be used singularly or in combination, or in combination with a reduced amount of a caloric or carbohydrate sweetener or natural flavorant such as, for example, sucrose. Preferred artificial sweeteners can include aspartame, cyclamates, artificial fruit flavor, and saccharin. Aspartame is 3-amino-N-(alpha-carboxyphenethyl) succinamic acid N-methyl ester, commonly known as NutraSweet. It is a dipeptide ester about 160 times sweeter than sucrose in aqueous solution. Aspartame is available from the NutraSweet Company, Chicago, Ill.

By "Cyclamate" herein is meant the sodium salt of cyclohexylsulfamic acid. It is about 30 times as sweet as refined cane sugar and can be used in the present invention alone or in combination with aspartame or other natural or artificial sweeteners.

Saccharin is 2,3-dihydro-3-oxobenzisosulfonazole. In dilute aqueous solution, it is about 500 times as sweet as sugar, and can be used herein alone or in combination with other sweeteners.

By "natural flavorant" herein is meant nutritive sweeteners, caloric sweeteners, natural fruit flavor, vanilla flavoring, vanilla bean extract, and the like.

The amount of artificial sweetener used in the artificially sweetened flavoring herein can vary according to the desired level of sweetness, the amount of residual lactose left after the UF treatment, the level of glucose or galactose, and the use of additional carbohydrate sweeteners or fruit.

Thus the cultured yogurt product derived from the UF treatment of skim milk followed by homogenization, pasteurization and enzymatic lactose reduction, is sweetened by the addition of an artificially sweetened flavoring. The inventors believe that it is heretofore unknown to combine these separate technologies to produce an acceptable low calorie, low lactose yogurt product. The product produced by the method of the present invention preferably has 60 to 70 calories per 170 grams of product, and a lactose level of less than 0.5% on a weight basis, and preferably less than 0.1%. In a most preferred embodiment, the yogurt produced by the present invention is essentially lactose-free, i.e., lactose is not detectable down to a level of about 0.06% by weight.

Commercially available, conventional low fat yogurt made without lactase treatment and without ultrafiltration, but with aspartame sweetener, generally has 90–95 calories per six ounces of product and a lactose content of about 6% by weight. One such product is Viva2 Nonfat yogurt, manufactured by Borden, Inc. By the present invention, using ultrafiltration, lactase treatment and aspartame sweetener, a yogurt product having 60–70 calories per six ounces (170 grams) of product is obtained, and which is essentially lactose free. Thus a reduction of the calorie content by approximately 33%, and the elimination of detectable lactose is achievable by the process of the present invention.

EXAMPLE 1

Ultrafiltration

Skim milk was processed through a DESAL ultrafiltration polysulfone membrane system containing a pore size of 10 to 500 Angstroms until the total solids level rose from the initial content of about 9% to 27.74% and exhibited a lactose level of 4.5 to 6% by weight. The retentate product was then rehydrated by the addition of water which resulted in a total solids level of 8.35% by weight, and a lactose level of about 1.5 to 1.6%.

EXAMPLE 2

Lactase Treatment

The rehydrated retentate obtained by the method of Example 1 was thickened by the addition with stirring of modified food starch Purity W by National Starch & Chemical, Inc., (0.75% by weight of the yogurt blend) and gelatin (250 bloom, 0.50% by weight of the yogurt blend). This mixture was heated to 140° F. and homogenized in a dual stage homogenization system having a 1500 psi first stage and a 500 psi second stage. The homogenized product was then pasteurized at 183° F. for thirty minutes, and then cooled to 106°–108° F. Pfizer's Neutral Lactase was added to the mixture at 0.1% by volume basis, followed by the addition of 1.5% by weight of a yogurt culture of *Lactobacillus bulgaricus* and *Streptococcus thermophilus* obtained from Chr. Hansen's Laboratory, Inc. The mixture was agitated and incubated at 106°–108° F. until the pH dropped to 4.50 at which time the yogurt mix was allowed to cool to 70°–75° F. At this time, the lactose level had dropped to below 0.06% by weight. Increasing the lactase level in the incubatingmixture to 0.25% by weight in another sample, resulted in lactose being undetectable in the yogurt produced.

EXAMPLE 3

Artificially Sweetened Yogurt With Added Flavoring Agents

The yogurt product produced by the method of Example 2 was sweetened by the addition of 0.03% by weight aspartame available from the NutraSweet Company. The aspartame was uniformly mixed into the yogurt product obtained from Example 2. Commercially available flavoring agents such as natural, natural and artificial, or artificial flavorants can also be added to the yogurt. The flavorings can be in liquid or powdered form and added at rates ranging from 0.15% to 2.00% by weight. The yogurt product thus produced had a caloric content of 60–70 calories per six ounces, compared to a conventional aspartame-sweetened yogurt prepared without lactase treatment and without ultrafiltration which generally has 90–95 calories per six ounces.

In addition, the product of the present invention has essentially no lactose remaining, there by making the product acceptable to lactose-intolerant individuals.

EXAMPLE 4

Sweetening And Flavoring Yogurt With Added Artificially Sweetened Yogurt Fruit Preparation The yogurt product produced by the method of Example 2 was sweetened and flavored in one step by the addition of 5% by weight artifIcially sweetened yogurt fruit preparation containing 0.6% aspartame. This product differs from that of Example 3 in that there is present in the finished yogurt small pieces of fruit which are suspended throughout and which provide fruit identity to a small degree.

The fruit preparation was supplied by Imperial Flavors, Winterhaven, Fla.

EXAMPLE 5

To the yogurt produced by the method of Example 3 was added a Microsized Soy Fiber, obtained from Howard Hall International, P.O. Box 199, CosCob, Conn.

06807 at 5% by weight. In this manner the calorie content of the artificially sweetened yogurt product was further reduced. Fruit flavoring can be added as in Example 4 above.

That which is claimed is:

1. A process for preparing reduced calorie, essentially lactose free, artificially sweetened yogurt product comprising:
   (a) concentrating skim milk by ultrafiltration whereby at least a portion of the lactose passes through into a permeate fraction and whereby the lactose level in a retentate fraction is decreased;
   (b) adding a lactase enzyme to the retentate fraction of step (a);
   (c) culturing the product of step (b) by adding a sufficient amount of a yogurt starter culture to the product, and allowing the mixture to incubate until the pH of the mixture is less than about 4.9;
   (d) adding an artificial sweetener to the cultured mixture of step (c).

2. The process of claim 1 wherein the ultrafiltration of step (a) increases the total solids level of the milk to about 30% on a dry weight basis.

3. The process of claim 1 wherein step (b) further comprises the addition of modified food starch and gelatin.

4. The process of claim 1 further comprising step (e) adding a suitable flavoring agent.

5. The process of claim 4 further comprising step (f) adding artificially sweetened yogurt fruit preparation.

6. The process of claim 1 wherein water is added to the retentate fraction obtained in step (a).

7. The process of claim 6 wherein the retentate to which water has been added is subjected to a temperature and pressure sufficient to homogenize the mixture.

8. The process of claim 6 wherein the retentate to which water has been added is subjected to a temperature sufficient to pasteurize the mixture.

9. The process of claim 1 wherein the incubation temperature of step (c) is in the range of from about 65° to 135° F.

10. The process of claim 1 wherein the incubation temperature of step (c) is in the range of from about 104° to 113° F.

11. The process of claim 1 wherein the lactase enzyme of step (b) is selected from beta-galactopyranosidase, beta-galatosidase, beta-D-galactoside galactohydrolase, and mixtures thereof, and is added in an amount sufficient to reduce the lactose content to less than 0.5% on a weight basis.

12. The process of claim 1 wherein the yogurt starter culture of step (c) is selected from the group consisting of *Lactobacillus bulgaricus* and *Streptococcus thermophilus* and mixtures thereof, and is present in an amount ranging from 0.5 to 3.0% by volume.

13. The process of claim 1 wherein the artificial sweetener of step (d) is selected from the group consisting of aspartame, cyclamate, and saccharin.

14. The process of claim 1 wherein the artificial sweetener of step (d) comprises a mixture of a material selected from the group consisting of aspartame, cyclamate, and saccharin, and a natural flavorant.

15. The process of claim 14 wherein the natural flavorant comprises a material selected from natural fruit flavor and vanilla.

16. The process of claim 14 wherein the natural flavorant is a material selected from the group consisting of fruit fiber, fruit pulp, fruit puree, fruit flavor, fruit extract, and fruit concentrate.

17. The process of claim 1 whereby the yogurt product produced has a caloric content of less than 90 calories per 170 grams of product.

18. The process of claim 1 whereby the yogurt product produced contains less than about 20% total solids on a dry weight basis, and has a calorie content of 60 to 70 calories per 170 grams of product.

19. The process of claim 1 whereby the yogurt produced has a lactose content of less than 0.1% by weight.

20. The product produced by the process of claim 1.

21. The process of claim 14 wherein step (b) further comprises the addition of modified food starch and gelatin.

22. The process of claim 1 further comprising the addition of artificial fruit flavor.

23. The process of claim 1 further comprising the addition of up to 5.0 percent by weight of soy fiber.

24. A process for preparing reduced calorie, essentially lactose free, artificially sweetened yogurt product comprising:
   (a) subjecting skim milk to ultrafiltration, whereby the skim milk is fractionated into a permeate fraction and a retentate fraction, wherein the lactose content in the retentate fraction is reduced relative to the initial lactose content of the skim milk;
   (b) adding water to the retentate fraction of step (a) whereby the total solids level is less than 11% by weight and the lactose content is less than 2.0% by weight;
   (c) homogenizing the product;
   (d) pasteurizing the product;
   (e) cooling the product of step (d) to a temperature sufficient to support enzyme activity and adding 0.01% to 0.06% by weight of a lactase enzyme;
   (f) adding a yogurt starter culture to the product of step (e) and incubating the mixture until the pH of the mixture reaches about 4.50 to 4.80; and
   (g) adding a sufficient amount of aspartame to sweeten the product of step (f) to a desired sweetness, wherein the yogurt product produced has 60 to 70 calories per 170 grams of product, and has a lactose content of less than 0.1% by weight.

25. The yogurt product produced by the process of claim 24.

26. An artificially sweetened yogurt product having 60 to 70 calories per 170 grams and a lactose content of less than 0.1% by weight.

* * * * *